(12) United States Patent
Karki et al.

(10) Patent No.: US 12,716,883 B1
(45) Date of Patent: Aug. 25, 2026

(54) REAL-TIME SOIL MOISTURE METER

(71) Applicant: Earth Scout, GBC, Minneapolis, MN (US)

(72) Inventors: Dipesh Karki, Minneapolis, MN (US); Troy Schmidtke, Minneapolis, MN (US); Christopher Burg, Minneapolis, MN (US); Michael Immer, Minneapolis, MN (US); Peder Lindberg, Fargo, ND (US); Scott Lawton, Eau Claire, WI (US)

(73) Assignee: EarthScout LLC, Brooklyn Park, MN (US)

( * ) Notice: Subject to any disclaimer, the term of this patent is extended or adjusted under 35 U.S.C. 154(b) by 290 days.

(21) Appl. No.: 18/630,221

(22) Filed: Apr. 9, 2024

(51) Int. Cl.
*A01G 7/00* (2006.01)
*G01N 33/24* (2006.01)

(52) U.S. Cl.
CPC ............ *G01N 33/246* (2013.01); *A01G 7/00* (2013.01); *G01N 33/245* (2024.05)

(58) Field of Classification Search
CPC .... G01N 33/246; G01N 27/223; G01N 33/24; G01N 22/04; G01N 33/245; G01N 27/048; G01N 5/045; G01N 27/221; G01N 33/0098; G01N 19/10; G01N 31/222; G01N 21/3554; G01N 27/121; G01N 25/56; G01N 2021/8466; G01N 21/84; G01N 21/359; G01N 27/00; G01N 1/08; G01N 5/025; G01N 15/08; G01N 27/226; G01N 9/24; G01N 27/041; G01N 21/17; G01N 33/42; G01N 21/25; G01N 27/22; G01N 21/55; G01N 23/06; G01N 2021/1793; G01N 27/228; G01N 23/005; G01N 23/203; G01N 27/04; G01N 27/225; G01N 1/44; G01N 2223/1013; G01N 13/00; G01N 21/3563; G01N 21/82; G01N 5/00; G01N 22/00; G01N 23/09; G01N 1/286; G01N 23/00; G01N 23/02; G01N 33/00; G01N 33/383; G01N 21/78; G01N 23/025; G01N 29/07; G01N 15/088; G01N 21/3151; G01N 25/20; G01N 27/02; G01N 33/36; G01N 33/442; G01N 1/28; G01N 15/0806; G01N 2223/616; G01N 27/605; G01N 5/02; G01N 15/0826; G01N 21/01; G01N 21/27; G01N 21/31; G01N 21/552; G01N 2201/06113; G01N 2223/613; G01N 24/081; G01N 27/227; G01N 33/18; G01N 33/34; G01N 9/36; G01N 23/20; G01N 25/18;

(Continued)

(56) References Cited

U.S. PATENT DOCUMENTS 4,918,375 A 4/1990 Malleki et al.
5,136,249 A 8/1992 White et al.

(Continued)

FOREIGN PATENT DOCUMENTS

| | | | | |
|---|---|---|---|---|
| BR | 102020024523 A2 * | 6/2022 | | G01R 11/04 |
| CN | 121499546 A * | 2/2026 | | |
| WO | WO-2013063135 A1 * | 5/2013 | | A01G 25/167 |

*Primary Examiner* — Andre J Allen
(74) *Attorney, Agent, or Firm* — Dietz Law Office LLC

(57) ABSTRACT

A meter for continuous real time monitoring of soil moisture or alternative logging data associated soil moisture. The meter includes determining a value associated with soil saturation, soil nitrogen mineralization, and growing degree units. These values are made available to the user real time.

17 Claims, 8 Drawing Sheets

(58) Field of Classification Search

CPC G01N 29/12; G01N 1/04; G01N 1/34; G01N 15/082; G01N 2223/647; G01N 2291/02845; G01N 27/043; G01N 33/10; G01N 1/2273; G01N 2013/003; G01N 21/274; G01N 23/2202; G01N 33/46; G01N 7/10; G01N 1/14; G01N 1/2205; G01N 1/38; G01N 13/04; G01N 2001/2282; G01N 2021/7766; G01N 25/00; G01N 25/58; G01N 27/025; G01N 27/12; G01N 17/00; G01N 2021/1797; G01N 21/14738; G01N 21/59; G01N 2291/0423; G01N 23/204; G01N 27/045; G01N 29/036; G01N 33/025; G01N 33/38; G01N 5/04; G01N 1/4022; G01N 2015/0813; G01N 2021/151; G01N 2021/4735; G01N 21/15; G01N 21/47; G01N 21/7703; G01N 21/8507; G01N 2223/063; G01N 2223/1016; G01N 2223/1063; G01N 2223/1066; G01N 2223/618; G01N 2223/635; G01N 2223/652; G01N 23/046; G01N 23/20008; G01N 27/028; G01N 27/046; G01N 29/022; G01N 29/11; G01N 29/2481; G01N 33/26; G01N 2001/1418; G01N 2021/155; G01N 2021/157; G01N 2021/158; G01N 2021/4709; G01N 2021/8887; G01N 2030/025; G01N 21/314; G01N 21/41; G01N 21/43; G01N 21/95684; G01N 2203/0048; G01N 2203/0236; G01N 2203/0682; G01N 2291/0238; G01N 2291/02441; G01N 2291/0253; G01N 23/20066; G01N 23/207; G01N 29/04; G01N 29/14; G01N 29/2418; G01N 3/12; G01N 1/20; G01N 1/24; G01N 1/42; G01N 13/02; G01N 15/06; G01N 15/075; G01N 17/04; G01N 2015/0034; G01N 2021/8883; G01N 21/00; G01N 21/35; G01N 21/3559; G01N 21/65; G01N 21/80; G01N 2201/129; G01N 2203/0075; G01N 2203/0676; G01N 2223/05; G01N 2223/053; G01N 2223/205; G01N 2223/301; G01N 2291/023; G01N 24/08; G01N 24/082; G01N 27/26; G01N 27/4165; G01N 27/72; G01N 29/24; G01N 31/221; G01N 33/02; G01N 33/182; G01N 33/241; G01N 33/3346; G01N 33/445; G01N 9/02; G01N 1/06; G01N 1/10; G01N 1/2035; G01N 1/2294; G01N 1/4044; G01N 1/4077; G01N 15/0205; G01N 17/006; G01N 17/02; G01N 19/00; G01N 2001/2285; G01N 2001/2866; G01N 2001/4033; G01N 2001/4088; G01N 2021/1765; G01N 2021/178; G01N 2021/558; G01N 21/171; G01N 21/3581; G01N 21/431; G01N 21/49; G01N 21/6486; G01N 2201/0238; G01N 2201/062; G01N 2201/1293; G01N 2203/0003; G01N 2203/0019; G01N 2223/303; G01N 2223/305; G01N 2223/3103; G01N 2223/402; G01N 2291/011; G01N 23/044; G01N 23/20083; G01N 23/222; G01N 23/2251; G01N 25/14; G01N 25/62; G01N 27/06; G01N 27/122; G01N 27/127; G01N 27/14; G01N 27/18; G01N 27/185; G01N 27/30; G01N 27/301; G01N 27/333; G01N 27/403; G01N 27/4077; G01N 27/4141; G01N 29/22; G01N 29/326; G01N 29/40; G01N 3/02; G01N 3/06; G01N 3/08; G01N 3/10; G01N 3/18; G01N 3/32; G01N 30/02; G01N 33/0004; G01N 33/0016; G01N 33/0047; G01N 33/0077; G01N 33/009; G01N 33/0091; G01N 33/222; G01N 33/243; G01N 33/6851; G01N 35/00; G01N 35/00693; G01N 35/0092; G01N 9/00; G01N 1/30; G01N 1/36; G01N 15/00; G01N 15/0266; G01N 15/0272; G01N 15/0893; G01N 2001/002; G01N 2001/366; G01N 2001/386; G01N 2001/4027; G01N 2009/024; G01N 2015/086; G01N 2021/0106; G01N 2021/0112; G01N 2021/3129; G01N 2021/354; G01N 2021/555; G01N 2021/557; G01N 2021/7723; G01N 2021/7759; G01N 2021/7773; G01N 2021/7783; G01N 2021/8411; G01N 2021/8416; G01N 2021/855; G01N 2021/8578; G01N 2035/0405; G01N 21/251; G01N 21/255; G01N 21/29; G01N 21/3103; G01N 21/3504; G01N 21/3586; G01N 21/64; G01N 21/718; G01N 21/77; G01N 21/774; G01N 21/85; G01N 21/95; G01N 2201/0214; G01N 2201/0221; G01N 2201/024; G01N 2201/0407; G01N 2201/0616; G01N 2201/0622; G01N 2201/0626; G01N 2201/064; G01N 2201/1211; G01N 2201/126; G01N 2203/0033; G01N 2203/0044; G01N 2203/0226; G01N 2203/0284; G01N 2203/0605; G01N 2223/04; G01N 2223/101; G01N 2223/614; G01N 2223/633; G01N 2223/649; G01N 2291/012; G01N 2291/0237; G01N 2291/0256; G01N 2291/02809; G01N 2291/02863; G01N 2291/044; G01N 2291/045; G01N 2291/106; G01N 23/083; G01N 23/16; G01N 25/005; G01N 27/023; G01N 27/07; G01N 27/205; G01N 27/416; G01N 27/4175; G01N 27/62; G01N 27/74; G01N 29/02; G01N 29/2437; G01N 29/30; G01N 29/348; G01N 29/42; G01N 29/44; G01N 3/068; G01N 3/14; G01N 3/20; G01N 3/24; G01N 3/42; G01N 3/567; G01N 31/162; G01N 31/20; G01N 31/22; G01N 33/0031; G01N 33/03; G01N 33/248; G01N 33/2823; G01N 33/48778; G01N 35/00871; G01N 35/0099; G01N 7/00; G01N 7/14; G01N 7/18; G01N 9/002

See application file for complete search history.

(56) References Cited

U.S. PATENT DOCUMENTS 5,420,517 A 5/1995 Skaling et al.
6,632,534 B2 10/2003 Skaling et al.

(56) References Cited

U.S. PATENT DOCUMENTS

| | | | |
|---|---|---|---|
| 6,978,794 B2 | 12/2005 | Dukes et al. | |
| 9,626,238 B2 | 4/2017 | Sheynblat et al. | |
| 9,690,426 B1 | 6/2017 | Eichwald | |
| 10,448,585 B2 | 10/2019 | Kundra et al. | |
| 10,509,019 B2 | 12/2019 | Lee | |
| 10,890,677 B2* | 1/2021 | Larue | A01G 25/167 |
| 11,275,949 B2 | 3/2022 | Chan et al. | |
| 11,360,644 B2 | 6/2022 | Karunumunai et al. | |
| 11,429,401 B2 | 8/2022 | Busekrus et al. | |
| 11,614,781 B1 | 3/2023 | Publicover et al. | |
| 2006/0256075 A1 | 11/2006 | Anastas et al. | |
| 2009/0212789 A1 | 8/2009 | Lin et al. | |
| 2015/0192557 A1* | 7/2015 | Abaffy | G01N 33/246 702/2 |
| 2018/0059014 A1 | 3/2018 | Ruback et al. | |
| 2018/0368339 A1 | 12/2018 | Van Der Lee | |
| 2020/0359583 A1 | 11/2020 | Buss | |
| 2021/0140908 A1 | 5/2021 | Van Houweling et al. | |
| 2022/0248617 A1 | 8/2022 | Buss | |
| 2023/0094121 A1 | 3/2023 | Eddaoudi et al. | |
| 2024/0402145 A1* | 12/2024 | Purdy | G01N 33/246 |
| 2026/0036565 A1* | 2/2026 | Anderson | G01N 33/246 |

* cited by examiner

REAL-TIME SOIL MOISTURE METER

CROSS-REFERENCE TO RELATED APPLICATIONS

Not Applicable.

FEDERAL SPONSORSHIP

Not Applicable

Joint Research Agreement

Not Applicable

TECHNICAL FIELD

This invention pertains generally to a handheld soil moisture meter that allows a grower to determine in real time certain soil conditions that affect plant growth and which allows a user to proactively adjust and make changes to growing practices. The meter of the present invention also allows a grower to navigate the user interface of the meter while wearing gloves. Further, the meter of the present invention provides the grower an option to log soil moisture data over time (associated with a particular field location) in order to determine field capacity and derive irrigation optimization, soil health maps, and nitrogen mineralization predictors. With this real time factual information, the grower is in a better position to make well-informed decisions regarding grower practices including modification of irrigation, fertilization, cultivation and other actions within the grower's control.

BACKGROUND

Over the years crop grower techniques for monitoring crop growth and field conditions have been altered to take into account various conditions such as soil saturation, soil nitrogen mineralization, and growing degree units. Often times a grower will be in the field wearing heavy work gloves while utilizing various electronic devices used to monitor field conditions. In order to navigate the user interface of these electronic devices, touch screens or additional control buttons have been provided. However, dirt, rain, or mud may cause product failures and work gloves have typically interfered with efficient navigation of prior crop growth and field monitoring electronic devices. Thus, there is a need for a rugged and robust soil moisture meter that allows navigation of a user interface of the moisture meter while wearing gloves.

SUMMARY

Embodiments according to aspects of the invention provides for a rugged handheld electronic device that allows a grower to navigate a user interface and choose between modes without the need to remove work gloves. The electronic device of the present invention may couple to soil moisture sensors, soil temp sensors, soil conductivity sensors and soil oxygen sensors to provide a grower with real time data and logged data corresponding to soil moisture, soil temp, soil conductivity, and soil oxygen levels. In a preferred embodiment of the present invention the handheld device couples to a TDR soil moisture sensor and the grower taps the device to choose between a real time mode and logged mode. The grower further taps the device to navigate through the user interface of the device.

These and other embodiments according to aspects of the invention include an apparatus for continuous real time monitoring and data logging of sensor outputs correlated with plant growth. The apparatus of the present invention has a housing, a display, an internal power supply, data ports, an internal electronic system, memory and accelerometers. The data input and output ports are adapted for electronically coupling to soil moisture sensors, soil temp sensors, soil conductivity sensors or soil oxygen sensors. The internal electronic system has an interactive user interface and memory electronically coupled to the internal electronic system. The accelerometers are electrically coupled to the electronic system, whereby a predetermined threshold output from the accelerometers (or accelerometer inputs to the electronic system) is required to activate and advance the interactive user interface.

According to aspects of the invention, the interactive user interface includes a meter mode and a logger mode. Further, the threshold output from the accelerometers may be determined by an accelerometer input amplitude detector that is electrically coupled with the electronic system. The display may be of a liquid crystal type. Also, the internal electronic system may include processing capabilities to determine a Field Capacity (FC) calculated from data outputs from soil moisture sensors. The calculated Field Capacity may be displayed on the LCD and may be saved in memory for future display and integration into future calculations. The internal electronic system is capable of telemetry and may link to external apps that further processes the real time and logged data from the moisture meter of the present invention. The telemetry may further include a remote data transmit module of known suitable construction. The moisture meter in accordance with aspects of the invention may further include a usb-c port electrically coupled to the internal electronic system and internal power supply. The usb-c port may be used to transmit data or provide a charge to the internal power supply. Further, a power switch may be coupled to the internal electronic system and internal power supply to activate and deactivate the moisture meter. Also, the power switch may include an LED backlight to assist the grower in deactivating the meter when in low light conditions.

In other embodiments according to aspects of the invention the apparatus for continuous real time monitoring and data logging of sensor outputs correlated with plant growth includes a housing, a display, an internal power supply, data input and output ports, an internal electronic system, a usb-c port, a power switch, memory and accelerometers electrically coupled to the internal electronic system. The data input output ports are adapted for electronically coupling to soil moisture sensors, soil temp sensors, soil conductivity sensors and/or soil oxygen sensors. The internal electronic system has an interactive user interface, wherein the interactive user interface includes a meter mode and a logger mode. Additionally, the internal electronic system includes an accelerometer input amplitude detector, wherein a predetermined input from the accelerometers is required to activate and advance the interactive user interface. Further, the memory is electronically coupled to the internal electronic system.

According to aspects of the invention the display may be of a liquid crystal type. Also, the internal electronic system determines a Field Capacity (FC) calculated from data outputs from soil moisture sensors and then displays the determined FC on the display. Additionally, the determined FC may be stored in memory and then displayed later or used to better access field capacity derived from future data. Also, the internal electronic system is capable of telemetry to thereby link to external apps.

In yet another embodiment according to aspects of the invention, the apparatus for continuous real time monitoring and data logging of sensor outputs correlated with plant growth includes a housing, a display of a liquid crystal type, an internal power supply, data input and output ports adapted for electronically coupling to sensors selected from the group consisting of soil moisture sensors, soil temp sensors, soil conductivity sensors and soil oxygen sensors, an internal electronic system having an interactive user interface, wherein the interactive user interface includes a meter mode and a logger mode and further wherein the internal electronic system includes an accelerometer input amplitude detector and further wherein the internal electronic system includes a remote data transmit module, memory electronically coupled to the internal electronic system, a usb-c port electrically coupled to the internal electronic system and internal power supply, a power switch coupled to the internal electronic system and internal power supply, and accelerometers, wherein a predetermined input from the accelerometers is required to activate and advance the interactive user interface. According to aspects of the invention the internal electronic system may determine a Field Capacity (FC) calculated from data outputs from soil moisture sensors and then displays the determined FC. Also, the internal electronic system may include resident programs to determine values associated with soil saturation, soil nitrogen mineralization, and growing degree units. Further, determining a value associated with soil saturation may include determining field capacity and plant water extraction limit and optionally also estimating available water holding capacity (AWC). Also, determining a value associated with soil nitrogen mineralization requires receiving data from a soil temperature sensor and a soil moisture content sensor.

The accompanying drawings, which are incorporated in and constitute a portion of this specification, illustrate embodiments of the invention and, together with the detailed description, serve to further explain the invention. The embodiments illustrated herein are presently preferred; however, it should be understood, that the invention is not limited to the precise arrangements and instrumentalities shown. For a fuller understanding of the nature and advantages of the invention, reference should be made to the detailed description in conjunction with the accompanying drawings.

DESCRIPTION OF THE DRAWINGS

In the various figures, which are not necessarily drawn to scale, like numerals throughout the figures identify substantially similar components.

DETAILED DESCRIPTION

Figure 1:
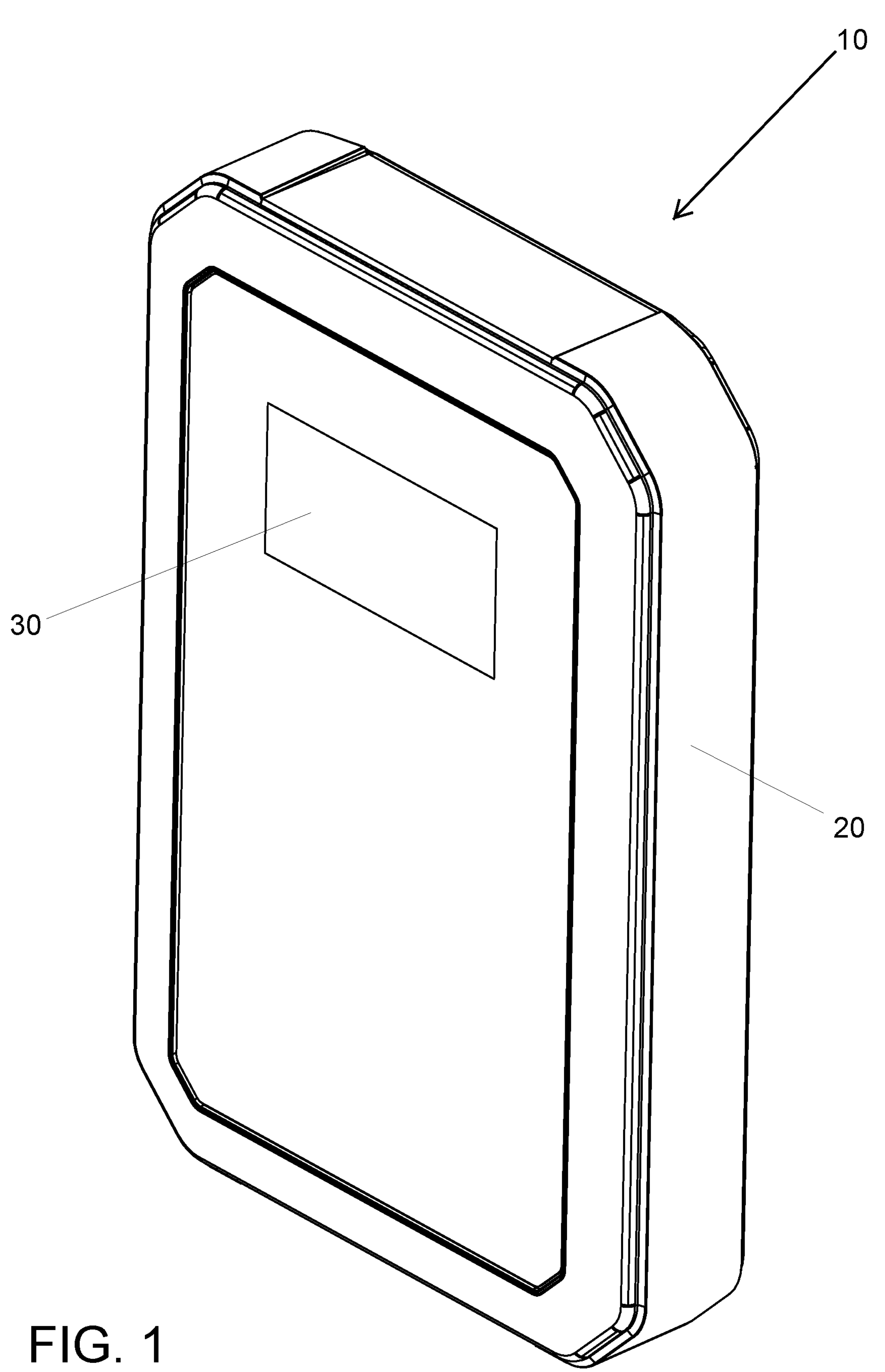
FIG. 1 is a front top perspective view of the meter in accordance with the present invention for continuous real time monitoring and data logging of sensor outputs correlated with plant growth.

The following description provides detail of various embodiments of the invention, one or more examples of which are set forth below. Each of these embodiments are provided by way of explanation of the invention, and not intended to be a limitation of the invention. Further, those skilled in the art will appreciate that various modifications and variations may be made in the present invention without departing from the scope or spirit of the invention. By way of example, those skilled in the art will recognize that features illustrated or described as part of one embodiment, may be used in another embodiment to yield a still further embodiment. Thus, it is intended that the present invention also cover such modifications and variations that come within the scope of the appended claims and their equivalents.

Aspects of the present invention include an apparatus and method that provides a crop grower with continuous real time output or logged output from a handheld moisture meter or device of the present invention. The moisture meter includes an electrical system with a user interface that the grower navigates by tapping the meter with sufficient force and duration to satisfy or exceed predetermined thresholds. Unlike capacitor-based touchscreens, the user interface navigation system of the present invention allows a grower to wear gloves while handling the moisture meter and navigating the user interface. The navigation system includes a plurality of accelerometers or force-based motion sensors of known suitable construction. The accelerometers or sensors are linked to an internal electronic system. Taps and other forces acting against the handheld meter are sensed and the electronic system discerns intentional taps by a user as opposed to a dropping or unintentional knocking of the meter.

Without limitation intended the accelerometers may be implemented as a micro electro-mechanical system (MEMS) device, a piezoelectric accelerometer, a piezoresistive accelerometer, a 3-axis silicon micromachined accelerometer, a surface-mount accelerometer, or combinations thereof. The accelerometers or sensors may be arranged and oriented such that force outputs from the sensors provides information related to a force on the handheld device associated with an X,Y,Z coordinate or other coordinate system or format. The accelerometers or sensors may be configured to measure, detect, or otherwise determine acceleration forces in at least two, but preferably three axes relative to a tap by a user. Further, in some embodiments, multiple accelerometers may be implemented, which may allow for cross-checking of two or more accelerometers against one another to enhance the reliability and accuracy of identification of acceleration force measurements in all three axes (e.g., X, Y, and Z, or pitch, yaw, and roll) and the filtering of unintentional forces acting against the handheld device.

In some embodiments, a processor of the electronic system may execute an algorithm stored in a memory of the electronic system to determine if the tap is intentional from a user. The algorithm may be of a learning algorithm type that becomes more robust in filtering unintentional forces the more the device is used. Without limitation, the learning algorithm utilized by the device may be of a supervised, unsupervised or reinforced learning algorithm type. In some embodiments, the learning algorithm may be configured to ignore unintentional forces detected by the sensors based upon the duration, magnitude or location of the force acting on the device. Thresholds may be established such that the processors monitor acceleration outputs from the accelerometers or sensors and either ignores the output or processes the output as an intentional tap by a user. By way of example, without limitation intended, the learning algorithm and thresholds established for the processor may determine characteristics of the acceleration forces (duration, amplitude, and location) to filter out unintended acceleration forces, reject erroneous inputs, correct an input, ignore inputs, provide error messages, request input confirmation or repeat, or combinations thereof. The processor may then advance or navigate through a menu displayed for the user based upon intentional taps by the user.

A display, such as a Liquid Crystal Display (LCD) or Light Emitting Diode (LED) display may be utilized to display the menu and other information to the user to assist the user in navigating the user interface. The menu and other information may include object "communications," "diagnostics," "displays," "I/O status," "load profile," and "power quality" to name just a few possible navigable functions within a user interface.

In accordance with aspects of the invention the handheld meter has an electronic system that includes (without limitation) integrated circuitry, processors, and memory. The processors are communicatively coupled to memory. The processors execute computer-executable program code stored in memory, accesses data stored in the memory, or both. Examples of a suitable processor are microprocessor, multi-core processor, an application-specific integrated circuit ("ASIC"), a field programmable gate array ("FPGA"), signal processor, controller, or any other suitable known processing device. The processor can include any number of processing devices or cores, including a single processing device. The functionality of the electronic system may be implemented in hardware, software, firmware, or a combination thereof. In some embodiments, the processor may include an on-board RAM, ROM, CMOS and/or FLASH memory storing processor-executable code, software, and/or firmware. The memory stores processor-executable instructions in a form of software and/or firmware that causes the processor to carry out the described functionality of the electronic system. Any of several formats of memory may be utilized to store data outputs or logged outputs including without limitation, non-transitory processor-readable medium, such as a hard drive, FLASH memory, solid-state memory card, external memory or other known suitable memory formats.

The instructions or program code may include processor-specific instructions generated by a compiler or an interpreter from code written in any suitable computer-programming language, including, for example, 15 C, C++, C#, Visual Basic, Linux, Java, or scripting language. The electronic system executes the computer-executable program instructions, that configure the processors to perform one or more of the operations described herein. The electronic system may also include a number of additional external or internal devices, such as input or output devices.

Further, in embodiments of the invention the handheld meter couples to a field sensor and either displays output from the sensor in real time mode or logs the output to memory. Although the handheld meter, in a preferred embodiment of the invention, couples to a Time Domain Reflectometry moisture sensor (TDR sensor), those skilled in the art will recognize that other soil moisture sensors, soil temp sensors, soil conductivity sensors or soil oxygen sensors may couple to the handheld meter without departing from the scope of the present invention. Outputs from these sensors may be used to determine and display values associated with soil saturation, soil nitrogen mineralization, and growing degree units. The user may further use this displayed information to adjust irrigation protocols or other grower practices.

The electronic system may further include a wireless relay that transmits and receives data with other devices within range of Bluetooth or wifi sinking. By way of example, the handheld moisture meter of the present invention may be sinked with a phone or tablet that includes additional processors and apps to further process data outputs from the moisture meter. Power management may be augmented with a solar panel charging unit and super capacitors allowing a user to choose a shorter time period for polling of each field unit (transmitting and receiving output and control commands of the field unit) without draining the battery below operable output.

The data output from the meter may include output data for soil nitrogen mineralization and soil moisture parameters. The output related to nitrogen mineralization is iterative over time and indicates to a grower when they don't need to add fertilization during the growing season. Over time a field may be monitored to determine fertilization needs. Further, as the data output becomes more robust, the amount of fertilizer needed at a given time may be adjusted to equal the total nitrogen need minus the cumulative produced nitrogen. The output from the soil probes coupled to the meter may be utilized to determine the cumulative produced nitrogen.

Additionally, the soil moisture outputs may be used to determine the desired irrigation needs, how much to irrigate, when to irrigate, and the expected return on investment dependent upon the actual irrigation schedule. Also, the processor may utilize the transmitted output, previous compiled outputs, user inputs, and/or reference data to compile data or information associated with soil moisture saturation, and soil nitrogen mineralization. This data or information is then made available and transmitted to the grower. The grower or user utilizes this output information to manually or automatically make adjustments to irrigation schedules, accessories, grower practices, and nitrogen mineralization predictors (to name just a few). Further, output data related to soil moisture and soil temperature observed at regular time intervals (e.g. 15 minutes) and at varying specified depths, collected over multiple growing seasons may be used to assess important soil moisture parameters, including field saturation (FS) moisture content (%), field capacity (FC) moisture content (%) and plant water extraction limit (PWEL) moisture content (%). These parameters can also be used to estimate other parameters, including plant available water holding capacity (AWC).

An exemplary methodology for estimating FS, FC and PWEL provides a simple approach that is quickly and easily interpreted. A spreadsheet is populated with two columns of data. The first column includes information about the time and date of data collection. The second column includes corresponding volumetric soil moisture measurements (%) from the sensor(s). Using data analysis of the spreadsheet, the data in the spreadsheet columns may be converted into a histogram of measured soil moisture values, with the y-axis for the histogram being frequency of observation and the x-axis being a "bin" for measured soil moisture. Bins are typically assigned values such as 4-6, 6-8, 8-10, 10-12 . . . 30-32, 32-34, 34-36, 36-38, 38-40, 40-42, 42-44, 44-46 (etc.), where the numbers represent a range of measured volumetric soil moisture values.

A value associated with Field saturation is simply determined by comparing the values in the various bins and identifying the bin with the largest observed value for soil moisture. The bin with the largest observed value is used to identify FS at or near that sensor. The FS for multiple sensors may be averaged to provide an average FS for the field. FC is determined by identifying the value of the bin with the highest frequency of observation (for the right hand peak when a bimodal distribution exists). Plant water extraction limit (PWEL) is not discernable in the case when long-term observations fail to include a period of drought. When the observation includes a drought event (low soil moisture for a period of time), the histogram will have a bimodal shape. The PWEL in this case is the value of the bin with the highest frequency of observation on the left hand peak of the histogram. Plant available water holding capacity (AWC) is simply determined by taking the difference between FC and PWEL. The FS and FC may be modified dependent on soil type and alternatively may be used to predict soil type. For example, if the resulting data for FC=18% and AWC=10% then this data suggests a soil texture of coarse sandy loam, loamy very fine sand or loamy fine sand. If the resulting data for FC=22% and AWC=12% this data would suggest a soil texture of sandy loam. Further, a resulting data of FC=34% would suggests a soil texture of loam.

Crops experience water stress when plant available water is depleted significantly. The allowable soil moisture depletion before irrigation is needed depends on the crop species, soil texture, and crop growth stage. A common guideline is to irrigate when plant available water is depleted by 50%. The moisture meter may be used identify when the soil moisture decreases below a predefined percent.

Field capacity is the soil moisture content attained after a soil is saturated and allowed to drain freely for two to three days. At field capacity, the soil has an optimum supply of water for the plant, along with an adequate supply of oxygen from gas filled pores. When irrigation is applied, the objective is often to add enough water to wet the soil up to field capacity. To estimate the depth of water that should be added by irrigation, it is necessary to know the initial soil moisture content ($\theta i$), the depth of soil (L), and the field capacity water content (FC). The depth of water added by irrigating (dw) is simply the depth of water held by the soil at field capacity (dwfc) minus the depth of water held by the soil initially before the onset of irrigation (dwi). The depth of water held by the soil at field capacity is $dwfc=FC*L$, while the depth of water held by the soil prior to irrigation is $dwi=\theta i*L$.

Nitrogen (N) mineralization is a process in which soil organic matter (SOM) is broken down by microorganisms, releasing organic nitrogen in the form of ammonium ($NH4+$) that can be taken up by crops. Ammonium can also be converted to nitrate-N($NO3$-N), which can be taken up by crops, leached through the soil or further converted to nitrogen gas through denitrification. Because of the challenges in estimating N mineralization rates, farmers making nitrogen fertilizer recommendations often ignore the contributions of SOM to N mineralization, resulting in over application of N fertilizer. Those skilled in the art are familiar with algorithms for estimating nitrogen mineralization in soil based on variations over time in soil temperature and soil moisture. As soil temperature increases, soil biological processes that include N mineralization increase exponentially before levelling off. This increase may be characterized to predict nitrogen mineralization dependent upon observed soil temperature and soil moisture. Soil moisture also affects N mineralization. Dry soils have slower mineralization rates than soils at optimum moisture contents. In similar fashion, excessively wet soils have slower mineralization rates than soils at optimum moisture contents. For improved generality, soil moisture content is represented in terms of the relative saturation(s), which is the soil moisture content divided by saturated soil moisture content. Saturated soil moisture content can be obtained using an analysis of meter outputs taking into account SOM. When the meter is set to the logging mode, the sensor data may be obtained (data polling) and stored. The data polling may occur, for example, between every 15 minutes to two hours depending upon the battery conservation protocol.

Figure 2:
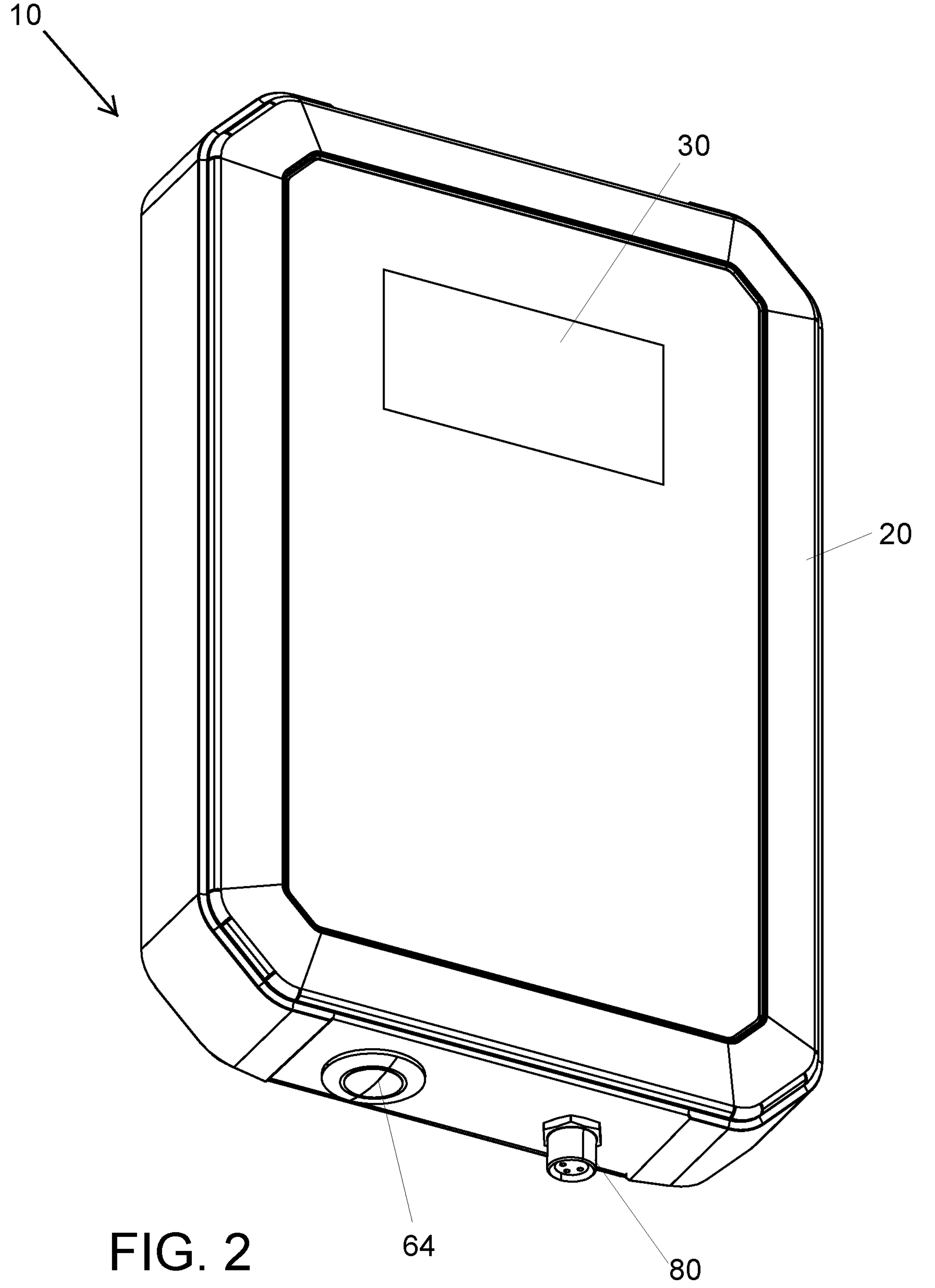
FIG. 2 is a front bottom perspective view of the meter of the type shown in FIG. 1.
Figure 3:
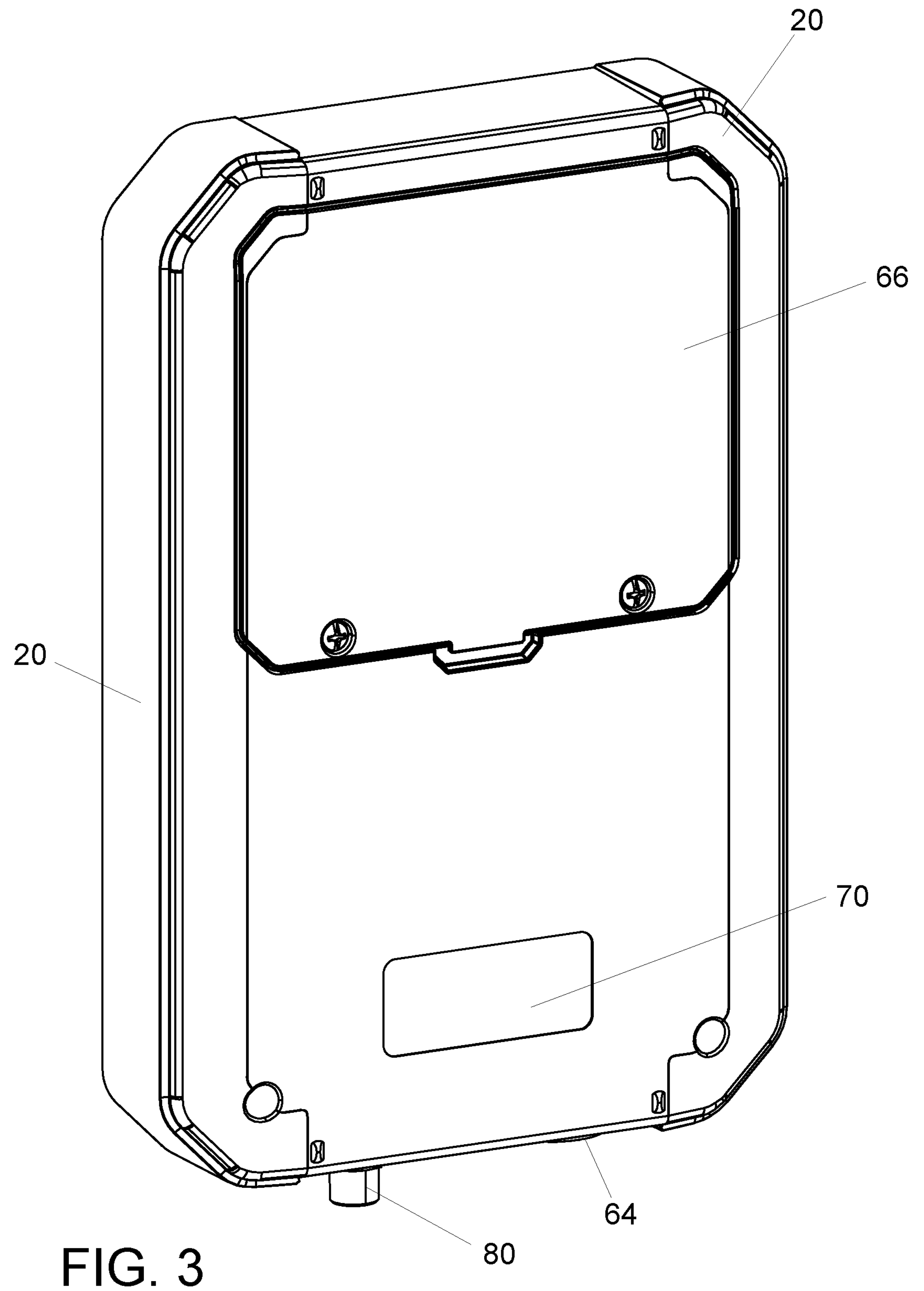
FIG. 3 is a back perspective view of a meter in accordance with the present invention.
Figure 5:
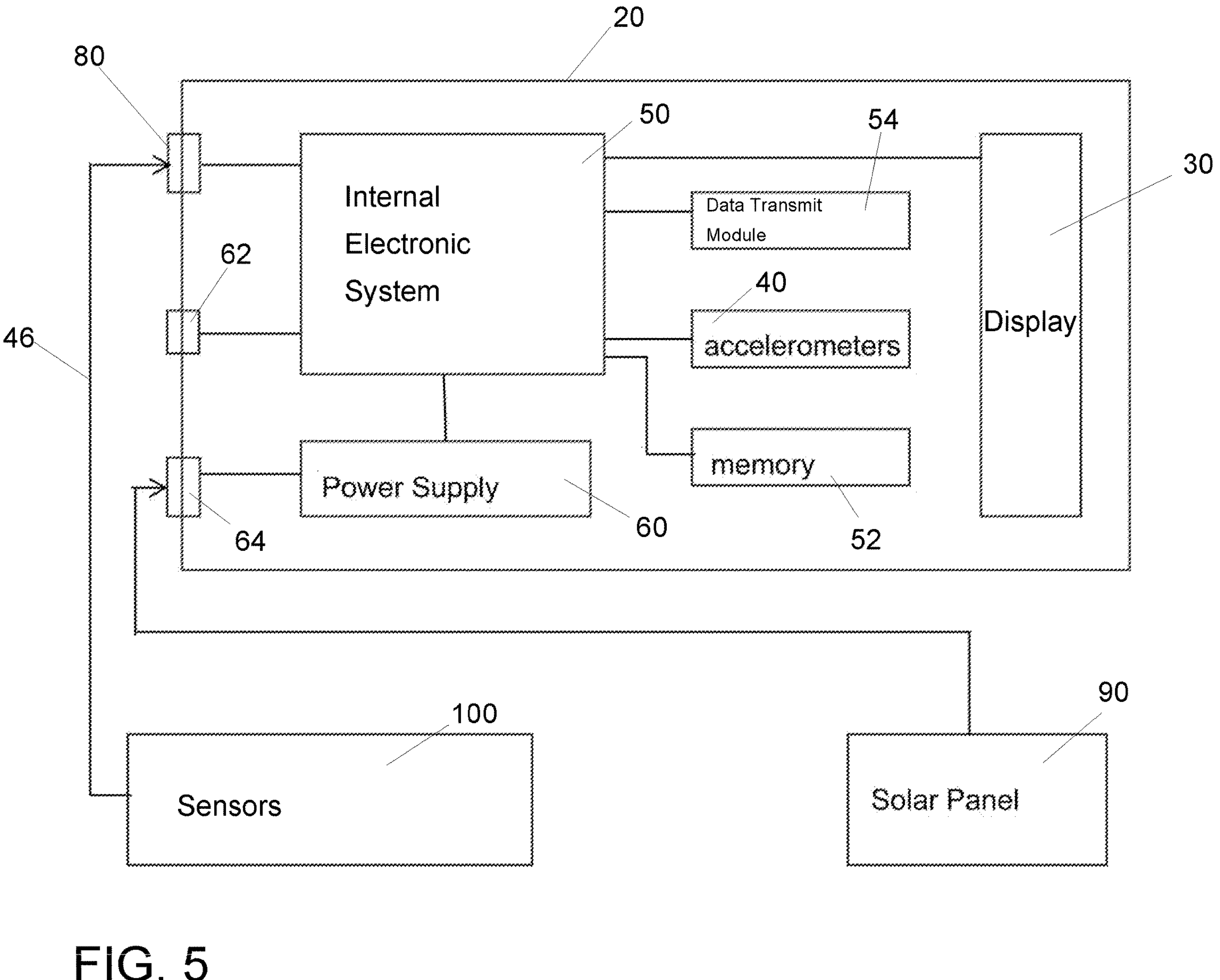
FIG. 5 is a schematic of components of a meter in accordance with the present invention.

Turning attention now to the Figures aspects of the moisture meter 10 of the present invention will be described in detail. Referring first to FIGS. 1-3, the meter 10 includes a housing 20, display 30. Coupled to the bottom of the housing 20 is an on/off power switch 64 and sensor coupling or data input/output port 80. The power switch 64 may further include an LED to assist the grower or user in locating the switch 64 in low light conditions. As seen in FIG. 5, a power port and usb-c port 62 is coupled to the bottom of the housing 20. The housing 20 further includes a display 30 sealed to a front opening in the housing. The back side of the housing includes a power access panel 66 that is fixed to the housing and includes a seal (not shown) sandwiched between the panel 66 and housing 30 to prevent moisture from migrating into the housing 30. The back side of the housing further includes an indent for placement of a QR code. The QR code may be used to allow a user to link the meter 10 to an app residing on a phone, tablet or other electronic device.

Figure 4:
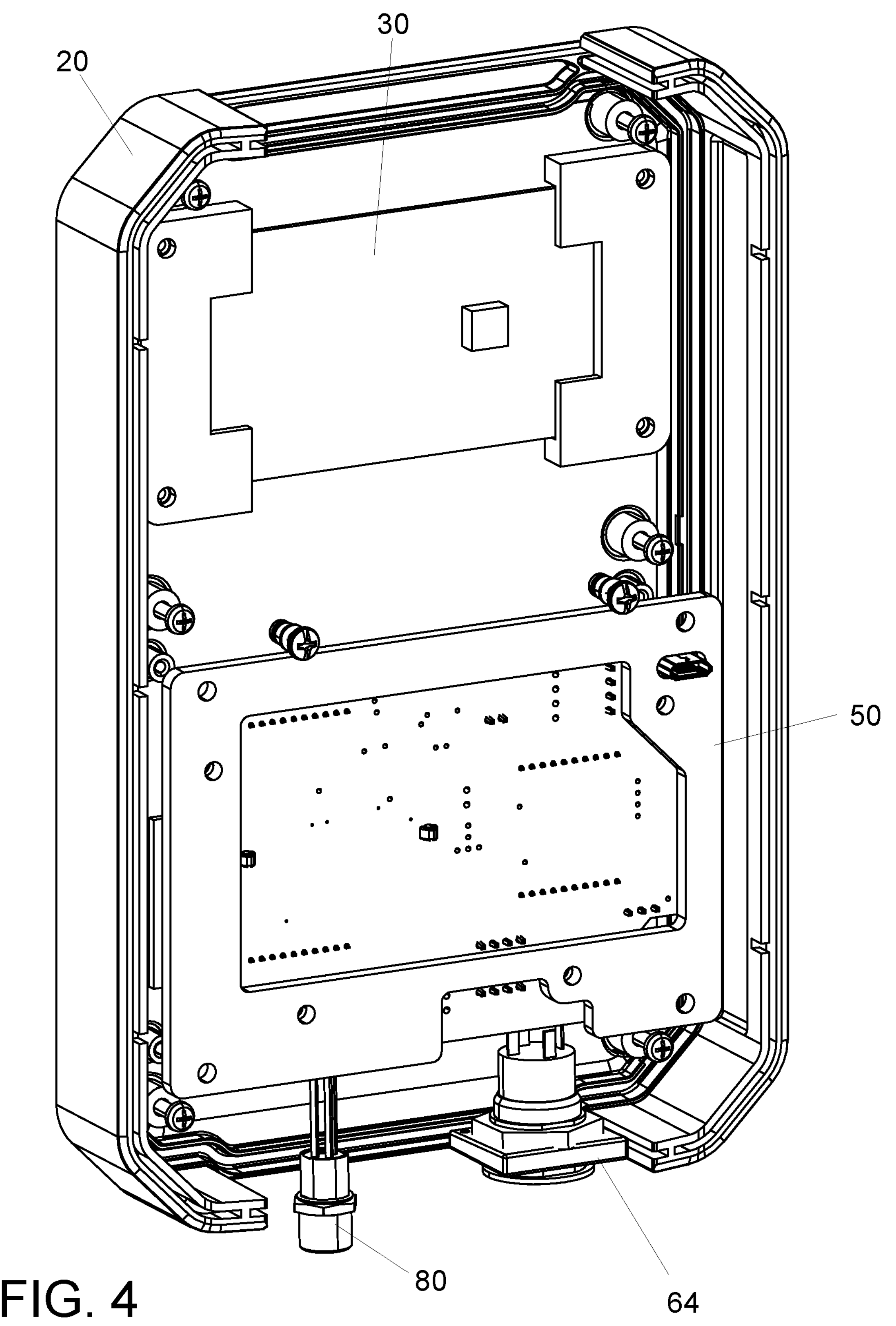
FIG. 4 is a partial sectional perspective view of a meter in accordance with the present invention.

FIGS. 4 and 5 illustrate the electronic system 50 and other components contained within the housing 20. The electronic system 50 is shown having a circuit board coupled to the housing. Those skilled in the art will appreciate that the circuit board may include an Integrated Circuit, CPU or other processing units, memory (RAM and ROM chips), and other required and known components. Electrical conduits 46 couple the electronic system 50 with a power supply 60, memory 52, data transmit module (wifi, Bluetooth or other telemetry component) 54, on/off power switch 64, input/output port 80, display 30, sensors 100, and accelerometers 40. The hand held unit may further couple to an external solar panel 90 to recharge power supply 60. Those skilled in the art will appreciate that the input/output port 80 may comprise a magnetic or quick release coupling of known suitable construction.

Figure 6:
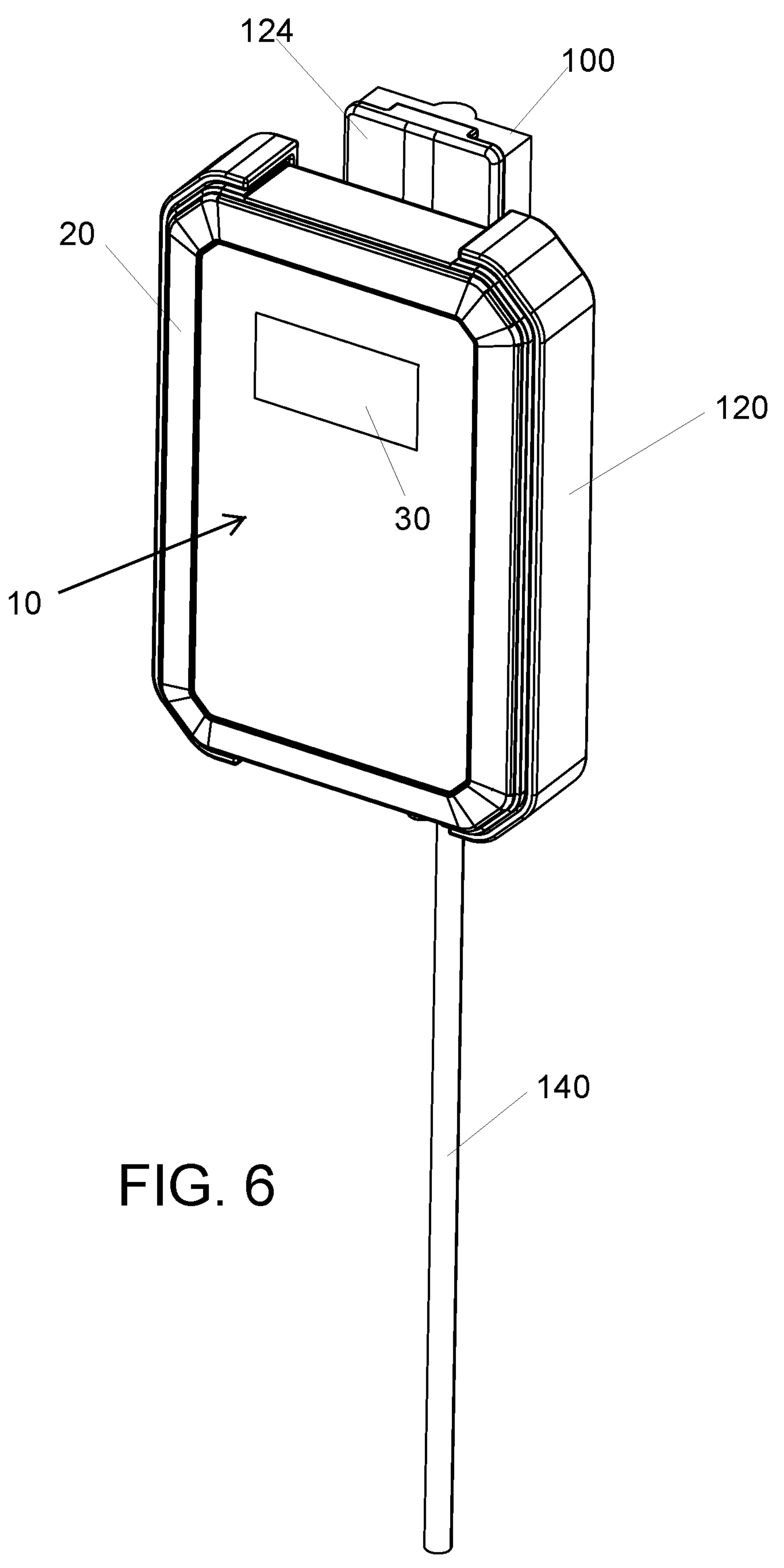
FIG. 6 is a perspective view of a meter of the present invention shown in a protective case and ready for installation in a field.
Figure 7:
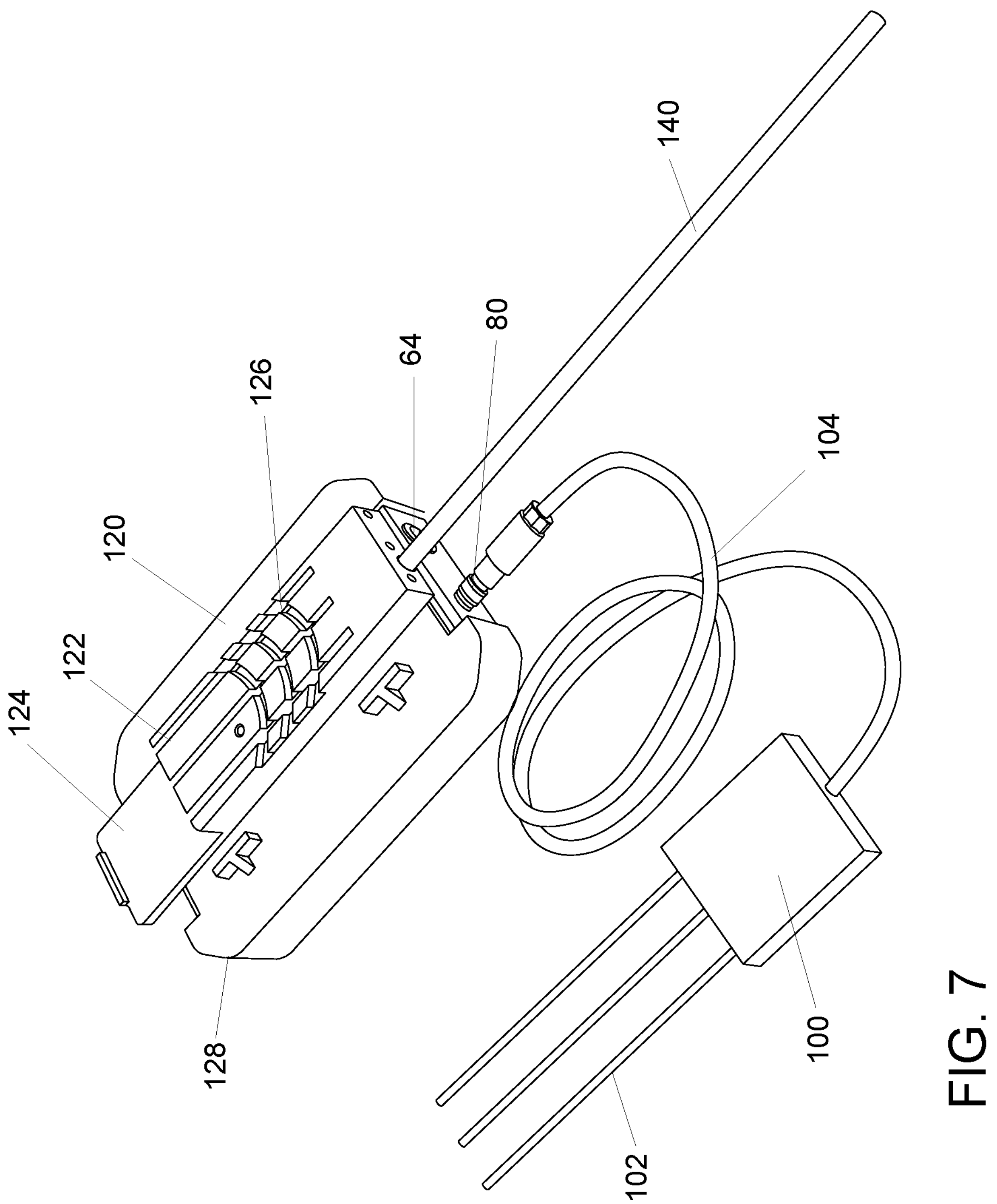
FIG. 7 is a back perspective view of a meter of the present invention shown in a protective case and coupled to a TDR soil moisture sensor.
Figure 8:
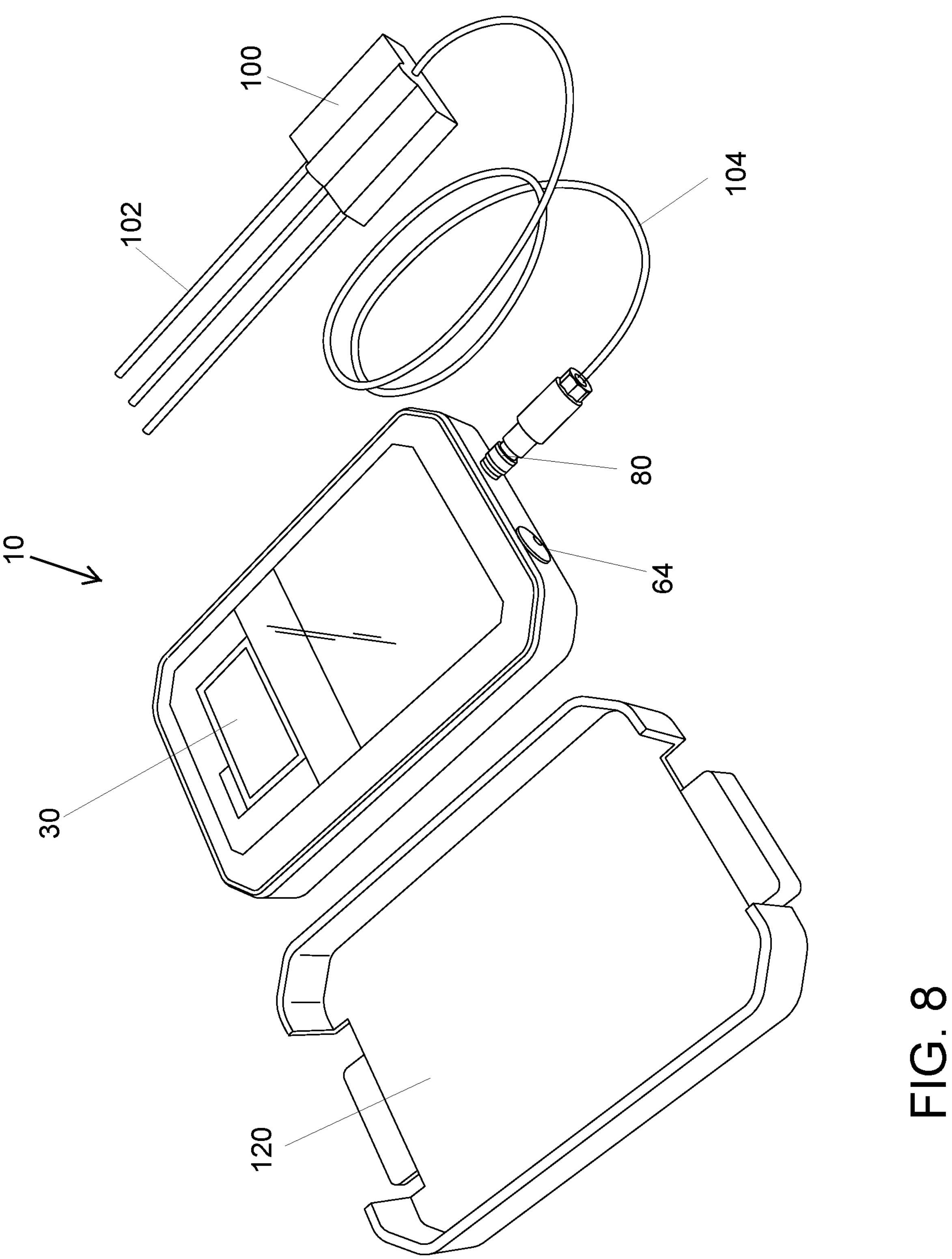
FIG. 8 is a front perspective view of a meter in accordance with the present invention and shown removed from a protective case and coupled with a TDR soil moisture sensor.

Referring to FIGS. 6-8 the meter 10 is illustrated in conjunction with a TDR moisture sensor 100. The sensor includes 3 prongs 102 that insert into slots 122 formed in the back of case 120 for storage. The case 120 further includes a tab 124 to retain the TDR sensor and also includes arced slots adapted to receive the sensor 100 transmit cable 104 in a preferred cable management orientation. The case 120 also includes side bumpers 128 that cushion and reduce impact to the meter 10, when the meter 10 is contained within the case 120. A rod 140 also couples to the case 120. In use, the user may insert the rod 140 into the ground such that the meter 10 is held in an upright position. The probe or sensor 100 may also be inserted into adjacent soil and coupled to the meter 10. Further, the user presses the on/off switch 64 to power up and activate the meter 10. Taps against the meter housing 20 with sufficient amplitude and duration to exceed preset thresholds will activate the user interface and allow the user to select a real time meter mode or a data logging mode. Additional navigation instructions and options are integrated with the processor and user interface.

These and various other aspects and features of the invention are described with the intent to be illustrative, and not restrictive. This invention has been described herein with detail in order to comply with the patent statutes and to provide those skilled in the art with information needed to apply the novel principles and to construct and use such specialized components as are required. It is to be understood, however, that the invention can be carried out by specifically different constructions, and that various modifications, both as to the construction and operating procedures, can be accomplished without departing from the scope of the invention. Further, in the appended claims, the transitional terms comprising and including are used in the open-ended sense in that elements in addition to those enumerated may also be present. Other examples will be apparent to those of skill in the art upon reviewing this document.

The following claims are incorporated into this description.

The invention claimed is:

1. An apparatus for continuous real time monitoring and data logging of sensor outputs correlated with plant growth, the apparatus comprising:
- a housing;
- a display;
- an internal power supply;
- data input and output ports adapted for electronically coupling to sensors selected from the group consisting of soil moisture sensors, soil temp sensors, soil conductivity sensors and soil oxygen sensors;
- an internal electronic system having an interactive user interface;
- memory electronically coupled to the internal electronic system;
- accelerometers for determining acceleration forces; and
- processors included with the internal electronic system that receive inputs from the accelerometers, wherein a predetermined input from the accelerometers is required to activate and advance the interactive user interface.

2. The apparatus as recited in claim 1, wherein the interactive user interface includes a meter mode and a logger mode.

3. The apparatus as recited in claim 1, wherein the internal electronic system includes an accelerometer input amplitude detector.

4. The apparatus as recited in claim 1, wherein the display is of a liquid crystal type.

5. The apparatus as recited in claim 2, wherein the internal electronic system determines a Field Capacity (FC) calculated from data outputs from soil moisture sensors and then displays the determined FC.

6. The apparatus as recited in claim 1, wherein the internal electronic system operates with telemetry.

7. The apparatus as recited in claim 1, wherein the internal electronic system includes a remote data transmit module.

8. The apparatus as recited in claim 1, further including a usb-c port electrically coupled to the internal electronic system and internal power supply.

9. The apparatus as recited in claim 1, further including a power switch coupled to the internal electronic system and internal power supply.

10. The apparatus as recited in claim 9, wherein the power switch is of the type that includes an LED backlight.

11. An apparatus for continuous real time monitoring and data logging of sensor outputs correlated with plant growth, the apparatus comprising:
- a housing;
- a display;
- an internal power supply;
- data input and output ports adapted for electronically coupling to sensors selected from the group consisting of soil moisture sensors, soil temp sensors, soil conductivity sensors and soil oxygen sensors;
- an internal electronic system having an interactive user interface, wherein the interactive user interface includes a meter mode and a logger mode and further wherein the internal electronic system includes an accelerometer input amplitude detector;
- memory electronically coupled to the internal electronic system; and
- accelerometers, wherein a predetermined input from the accelerometers is required to activate and advance the interactive user interface.

12. The apparatus as recited in claim 11, wherein the display is of a liquid crystal type.

13. The apparatus as recited in claim 12, wherein the internal electronic system determines a Field Capacity (FC) calculated from data outputs from soil moisture sensors and then displays the determined FC.

14. The apparatus as recited in claim 11, wherein the internal electronic system operates with telemetry.

15. An apparatus for continuous real time monitoring and data logging of sensor outputs correlated with plant growth, the apparatus comprising:
- a housing;
- a display of a liquid crystal type;
- an internal power supply;
- data input and output ports adapted for electronically coupling to sensors selected from the group consisting of soil moisture sensors, soil temp sensors, soil conductivity sensors and soil oxygen sensors;
- an internal electronic system having an interactive user interface, wherein the interactive user interface includes a meter mode and a logger mode and further wherein the internal electronic system includes an accelerometer input amplitude detector and further wherein the internal electronic system includes a remote data transmit module;
- memory electronically coupled to the internal electronic system;
- a usb-c port electrically coupled to the internal electronic system and internal power supply;
- a power switch coupled to the internal electronic system and internal power supply; and
- accelerometers, wherein a predetermined input from the accelerometers is required to activate and advance the interactive user interface.

16. The apparatus as recited in claim 15, wherein the internal electronic system determines a Field Capacity (FC)

calculated from data outputs from soil moisture sensors and then displays the determined FC.

17. The apparatus as recited in claim 15, wherein the power switch is of the type that includes an LED backlight.

* * * * *